(12) United States Patent
Cantor

(10) Patent No.: US 7,465,703 B1
(45) Date of Patent: Dec. 16, 2008

(54) METHODS AND KITS USEFUL FOR GUIDING OSTEOPOROSIS RELATED THERAPY

(75) Inventor: Thomas L. Cantor, El Cajon, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 513 days.

(21) Appl. No.: 10/956,760

(22) Filed: Oct. 1, 2004

Related U.S. Application Data

(60) Provisional application No. 60/508,057, filed on Oct. 1, 2003.

(51) Int. Cl.
*A61K 38/29* (2006.01)
*C12Q 1/00* (2006.01)

(52) U.S. Cl. .............................................. 514/2; 435/4
(58) Field of Classification Search ........................ None
See application file for complete search history.

(56) References Cited

U.S. PATENT DOCUMENTS

| | | | |
|---|---|---|---|
| 4,423,037 A * | 12/1983 | Rosenblatt et al. ............. 514/12 |
| 4,968,669 A | 11/1990 | Rosenblatt et al. ............. 514/12 |
| 5,093,233 A | 3/1992 | Rosenblatt et al. ......... 435/7.21 |
| 5,317,010 A | 5/1994 | Pang et al. ..................... 514/12 |
| 5,382,658 A | 1/1995 | Kronis et al. ................ 530/397 |
| 5,723,577 A | 3/1998 | Dong .......................... 530/324 |
| 2003/0138858 A1 | 7/2003 | Cantor ........................ 435/7.9 |
| 2004/0067526 A1 | 4/2004 | Cantor ........................ 435/7.1 |

OTHER PUBLICATIONS

Messer W. S. "Vasopressin and Oxytocin" [online], Apr. 3, 2000, pp. 1-5, [retrieved on Jul. 3, 2007]. Retrieved from the internet: <URL:http://www.neurosci.pharm.utoledo.edu/MBC3320/vasopressin.htm>.*
Vasikaran et al. "The Role of Biochemical Markers of Bone Turnover in Osteoporosis Management in Clinical Practice," Clin. Biochem. Rev., 2006, vol. 27m 119-120.*
U.S. Appl. No. 10/617,489, Cantor, filed Aug. 2003.
U.S. Appl. No. 10/664,263, Cantor, filed Sep. 2003.
Bergstrom et al., Arch. Biochem. Biophys. (2000) 373:231-241.
Black et al., New England J. Med. (2003) 349:1207-1215.
Divieti et al., Endocrinology (2002) 143(1):171-176.
Divieti et al., J. Bone Miner. Res. (2001) Suppl 1:S307.
Faugere et al., J. Am. Soc. Nephrol (2001) 12:764A.
Faugere et al., Kidney Int. (2001) 60:1460-1468.
Grauer et al., Dtsch. Med. Wochenschr. (1994) 119:507-510.
LePage et al., Clin. Chem. (1998) 44:805-810.
Van Beck et al., Biochem. Biophys. Res. Commun. (1999) 264:108-111.
Watson et al., Molecular Biology of the Gene, 4th ed., (1987) p. 224.
Whyte et al., New England J. Med. (2003) 349:457-463.
Zikan and Stepan, Clin. Chim. Acta (2002) 316:63-69.

* cited by examiner

*Primary Examiner*—Cecilia Tsang
*Assistant Examiner*—Christina Marchetti Brad
(74) *Attorney, Agent, or Firm*—Morrison & Foerster LLP

(57) ABSTRACT

The present invention relates to methods and kits useful for guiding the administration of a therapeutic agent in a subject afflicted with, or believed to be afflicted with osteoporosis.

13 Claims, 1 Drawing Sheet

SEQUENCE LISTING

<160> NUMBER OF SEQ ID NOS: 2

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asn Lys Ala Asp Val Asn Val Leu Thr Lys
65                  70                  75                  80

Ala Lys Ser Gln

<210> SEQ ID NO 2
<211> LENGTH: 6
<212> TYPE: PRT
<213> ORGANISM: Homo sapiens

<400> SEQUENCE: 2

Ser Val Ser Glu Ile Gln
1               5

METHODS AND KITS USEFUL FOR GUIDING OSTEOPOROSIS RELATED THERAPY

PRIORITY CLAIM

This application claims priority benefit of U.S. Provisional Patent Application No. 60/508,057, filed Oct. 1, 2003 under 35 U.S.C. § 119(e), the content of which is incorporated by reference in its entirety.

TECHNICAL FIELD

The present invention relates to methods and kits useful for guiding administration of a therapeutic agent in a subject afflicted with, or believed to be afflicted with osteoporosis.

BACKGROUND OF THE INVENTION

Calcium plays an indispensable role in cell permeability, the formation of bones and teeth, blood coagulation, transmission of nerve impulse, and normal muscle contraction. The concentration of calcium ions in the blood is, along with calcitriol and calcitonin, regulated mainly by parathyroid hormone (PTH). Extracellular calcium levels are directly affected by PTH through calcium uptake in kidney tubule cells and calcium transport to or from bone. Although calcium intake and excretion may vary, PTH serves through feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are particularly at risk for idiopathic osteoporosis (postmenopausal or Type I osteoporosis). Another high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, and oophorectomy.

The complete or whole form of human PTH, (hPTH), is a unique 84 amino acid peptide (SEQ ID NO: 1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, hPTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See LePage, R., et al., *Clin. Chem.* (1998); 44: 805-810.)

The present invention is based, in part, on the premise that there are two types of hormones (both secreted by the parathyroid gland) that are antagonists which exert control over the rate of bone turnover. CAP (cyclase activating PTH or PTH agonist), e.g., $PTH_{1-84}$, operating through the PTH/PTHrp receptor accelerates bone turnover, and CIP (cyclase inactive PTH or PTH antagonist), frequently comprised of $PTH_{7-84}$, operates through a C terminal PTH receptor and decelerates bone turnover.

A variety of therapeutic agents are available for the treatment of osteoporosis, and some agents are more appropriate for some subjects than others. As further described herein, treatment with one agent versus another may have detrimental health related implications. Thus, treatment options for osteoporosis patients should be individualized to maximize therapeutic potential and to minimize detrimental health related implications resulting from poor therapeutic agent choices. The present invention addresses this and other related needs in the art.

The present description further contemplates kits in accordance with the methods provided herein. Such kits comprise materials and instructions suitable for performing the present methods and the like.

SUMMARY OF THE INVENTION

In one embodiment, a method is provided for guiding the administration of a therapeutic agent in a subject afflicted with, or believed to be afflicted with, osteoporosis, comprising: obtaining a first biological sample from said subject; administering to said subject a parathyroid hormone (PTH) based therapeutic composition; obtaining a second biological sample from said subject after administration of said therapeutic; evaluating said first and second samples for a PTH antagonist level, and optionally a total PTH level or a PTH agonist level; and wherein if the PTH antagonist is present at a higher level in the second sample versus the first sample, and/or if the ratio of the PTH antagonist versus the total PTH level (or the PTH agonist level) is higher in the second sample versus the first sample, then the subject may be considered a candidate for treatment with said PTH based therapeutic composition, and wherein if the PTH antagonist is present at the same or lower level in the second sample versus the first sample, and/or if the ratio of the PTH antagonist level versus total PTH level (or the PTH agonist level) is the same or lower in the second sample versus the first sample, then the subject is not considered a candidate for treatment with said PTH based therapeutic composition. In a frequent embodiment, the first and second samples are evaluated for two or more parameters comprising the PTH antagonist level, the total PTH level and/or the PTH agonist level, and at least two of the parameters are compared; frequently such comparison of the two or more parameters is in the form of a ratio or proportion.

In a frequent embodiment, the PTH based therapeutic composition comprises $PTH_{1-34}$, $PTH_{1-84}$ or $PTH_{7-84}$. Moreover, the PTH based therapeutic composition often comprises a PTH agonist or a PTH antagonist. Frequently, the PTH antagonist comprises $PTH_{7-84}$. On occasion, the PTH agonist comprises $PTH_{1-84}$. Also on occasion, the PTH antagonist comprises $PTH_{7-84}$ and the PTH agonist comprises $PTH_{1-84}$.

In another frequent embodiment, a time period exists between the administering step and obtaining the second biological sample. Frequently, the time period is about 45 minutes. Although on occasion, the time period may range between about 5 minutes to about 4 hours, or more. On occasion a time period exists between obtaining the first sample and the administering step. Also on occasion, any one or more of the steps of the present methods are performed at different locations and/or by different people or entities.

In another frequent embodiment, the present method(s) further comprise(s) evaluating the first and second samples for the presence of therapeutic inactivating antibodies specific for the therapeutic composition. Also frequently, if therapeutic inactivating antibodies specific for the PTH based therapeutic agent are present, the subject is not considered a candidate for treatment with the PTH based therapeutic composition.

In an occasional embodiment, the above embodiments may further comprise deciding to initiate, terminate, or adjust the level of administration of a therapeutic agent to the subject based on the results of the evaluating step. On occasion, the therapeutic agent comprises a PTH based therapeutic agent. Also on occasion, the therapeutic agent comprises a bisphosphonate, salmon calcitonin, calcium citrate, a calcimimetic (e.g., cinacalcet HCl or AMG-073, available from NPS Pharmaceuticals), a PTH based therapeutic agent (e.g., $PTH_{1-84}$, $PTH_{1-34}$, $PTH_{7-84}$, or alternatively, a PTH agonist or a PTH antagonist), or a combination thereof. In an occasional embodiment, the subject is determined to not be a candidate for treatment with a PTH based therapeutic agent and a decision is made to administer a therapeutic agent selected from a bisphosphonate, salmon calcitonin, calcium citrate, a calcimimetic, or a combination thereof. In another occasional embodiment, the subject is determined to be a candidate for treatment with a PTH based therapeutic agent, and a decision is made to administer a PTH based therapeutic agent comprising a PTH agonist or PTH antagonist.

In a further frequent embodiment, the above methods further comprise: obtaining a third biological sample from said subject after obtaining the second biological sample; and evaluating said third sample for a PTH antagonist level, and optionally a total PTH level or a PTH agonist level; wherein if the PTH antagonist is present at a higher level in the third sample versus the first sample, and/or if the ratio of the PTH antagonist versus the total PTH level (or the PTH agonist level) is higher in the third sample versus the first sample, then the subject may be considered a candidate for treatment with said PTH based therapeutic composition, and wherein if the PTH antagonist is present at the same or lower level in the third sample versus the first sample, and/or if the ratio of the PTH antagonist level versus total PTH level (or the PTH agonist level) is the same or lower in the third sample versus the first sample, then the subject is not considered a candidate for treatment with said PTH based therapeutic composition. In a frequent embodiment, the first and third samples are evaluated for two or more parameters comprising the PTH antagonist level, the total PTH level and/or the PTH agonist level, and at least two of the parameters are compared; frequently such comparison of the two or more parameters is in the form of a ratio or proportion. Also frequently, a second time period exists between obtaining the second biological sample and obtaining the third biological sample. Also frequently, the second time period is about 45 minutes. Although on occasion, the time period may range between about 5 minutes to about 4 hours, or more.

In a further embodiment, a kit is provided for guiding administration of a therapeutic agent in a subject afflicted with, or believed to be afflicted with, osteoporosis, said kit comprises: a) means for obtaining a biological sample from a subject; b) a parathyroid hormone (PTH) based therapeutic composition; and c) means for evaluating said sample for a PTH antagonist level, a total PTH level and/or a PTH agonist level.

DETAILED DESCRIPTION OF THE INVENTION

Figure 1:
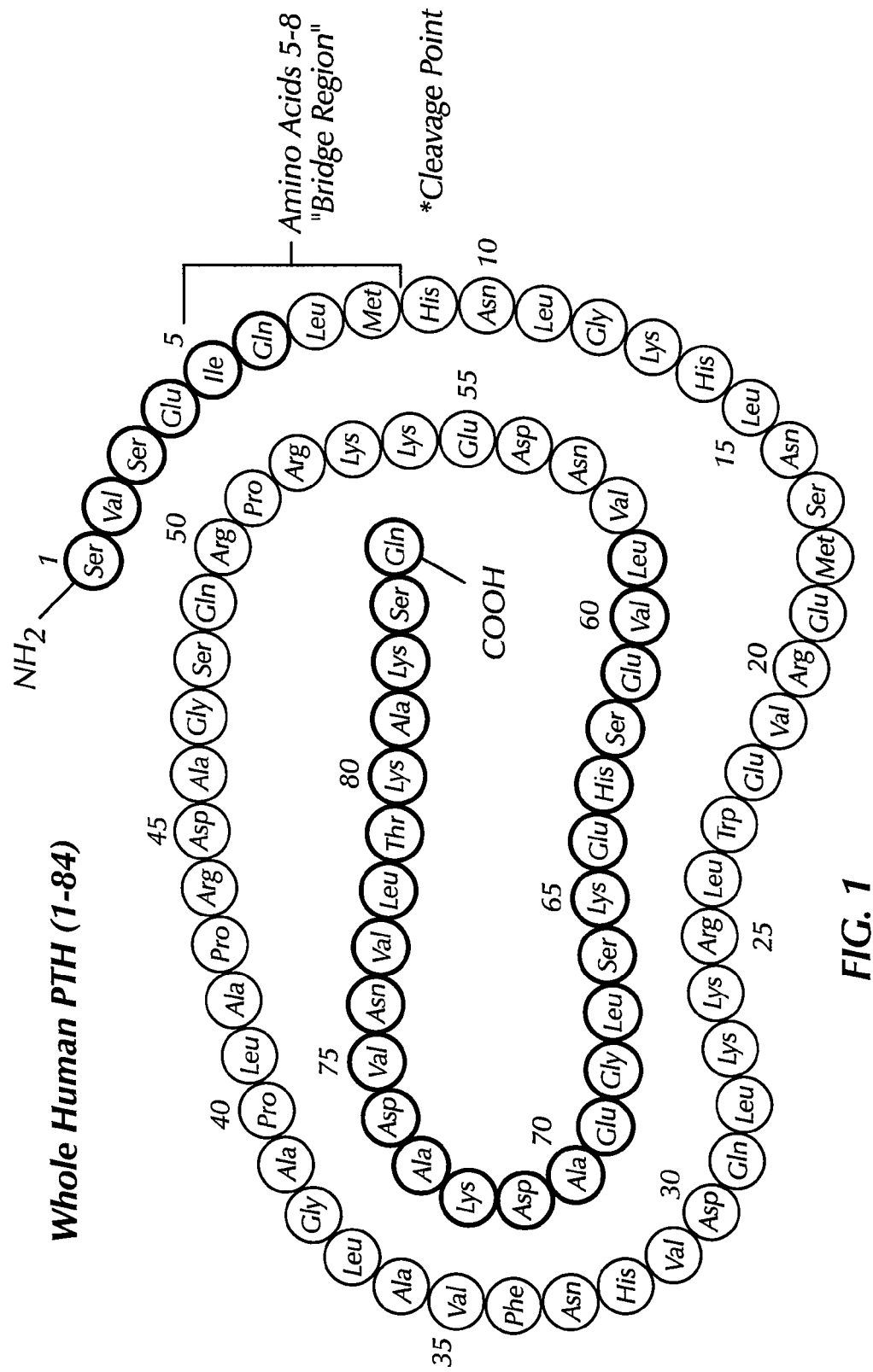
FIG. 1 is a diagrammatic view of hPTH (SEQ ID NO:1).

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "parathyroid hormone (PTH) antagonist" or "CIP" refers to a PTH fragment or derivative that counters the effect of a PTH agonist or otherwise lacks PTH agonist activity. It is intended to encompass a PTH antagonist with conservative amino acid substitutions that do not substantially alter its activity. Suitable conservative substitutions of amino acids are known to those of skill in this art and may be made generally without altering the biological activity of the resulting molecule. See, e.g., U.S. application Ser. No. 10/265,276, filed Oct. 3, 2002. Those of skill in this art recognize that, in general, single amino acid substitutions in non-essential regions of a polypeptide do not substantially alter biological activity (see, e.g., Watson, et al. MOLECULAR BIOLOGY OF THE GENE, 4th Edition, 1987, The Benjamin/Cummings Pub. co., p. 224). For example, a PTH antagonist may contain amino acid residue substitutions or modifications such as: $His_{25}$, $His_{26}$, $Leu_{27}$, (U.S. Pat. No. 5,382,658); $Tyr_{34}$, $D-Trp_{12}$, $Nle_{8,18}$, desamino($Nle_{8,18}$), $Lys_{13}$ modified in the epsilon-amino acid group by N,N-diisobutyl or 3-phenylpropanoyl (U.S. Pat. No. 5,093,233); $Gly_{12}$ substituted by D-Trp, L-Trp, L- or D-α- or β-naphthylalanine, or D- or L-α-MeTrp (U.S. Pat. No. 4,968,669); the amino acid residue at positions 7, 11, 23, 24, 27, 28, or 31 being cyclohexylalanine, the amino acid residue at position 3, 16, 17, 18, 19, or 34 being α-aminoisobutyric acid, the amino acid residue at position 1 being a, β-diaminopropionic acid, the amino acid residue at position 27 being homoarginine, the amino acid residue at position 31 being norleucine (U.S. Pat. No. 5,723,577); each of $Arg_{25}$, $Lys_{26}$, $Lys_{27}$ being substituted with Ala, Asn, Asp, Cys, Gln, Glu, Gly, His, Ile, Leu, Met, Phe, Pro, Ser, Thr, Trp, Tyr or Val (U.S. Pat. No. 5,317,010); and a combination thereof. Suitable PTH antagonists may be derived from a variety of mammal species.

The N-terminal amino acid residue of the PTH antagonist can start at any position spanning position 2 through position 33 of the $PTH_{1-84}$ molecule. For example, the N-terminal amino acid residue of the PTH antagonist can start at position 2 of $PTH_{1-84}$. The C-terminal amino acid residue of the PTH antagonist can end at any position spanning position 35 through position 84 of the $PTH_{1-84}$. For example, the C-terminal amino acid residue of the PTH antagonist can end at position 84 of the $PTH_{1-84}$.

As used herein, "parathyroid hormone (PTH) agonist" or "CAP" refers to the complete molecule of PTH or a fragment, derivative or analog thereof that stimulates osteoclasts formation and bone turnover to increase blood calcium levels. PTH agonist further refers to peptides which have PTH agonist properties. Other names of PTH include parathormone and parathyrin. For purposes herein, the name "parathyroid hormone (PTH)" is used herein, although all other names are contemplated. It is intended to encompass PTH agonist with conservative amino acid substitutions that do not substantially alter its biological activity. Suitable conservative substitutions of amino acids are known to those of skill in this art and may be made generally without altering the biological activity of the resulting molecule. See, e.g., U.S. application Ser. No. 10/265,276, filed Oct. 3, 2002. Those of skill in the art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. co., p. 224). PTH agonist assay values may be obtained by measuring a sample with a Scantibodies Whole PTH Assay or a Scantibodies CAP Assay or a $3^{rd}$ generation PTH Assay or a Nichols BioIntact PTH assay or an Immutopics Human Bioactive PTH assay. Suitable PTH agonists may be derived from a variety of mammal species.

The N-terminal amino acid residue of a PTH agonist may start at position 1 of the $PTH_{1-84}$ molecule. The C-terminal amino acid residue of said PTH agonist can end at any position spanning from position 34 through position 84 of said $PTH_{1-84}$. For example, the C-terminal amino acid residue of the PTH agonist can end at position 84 of the $PTH_{1-84}$. Notably, the PTH agonist can have any suitable length provided that it maintains its agonizing activity.

As used herein, the terms "total PTH," "intact PTH" and "total intact PTH" are interchangeable and refer to an assay directed at measuring PTH agonist and PTH antagonist levels. As used herein, the term "total PTH" refers to a total accounting of whole PTH levels in addition to PTH fragment levels. Moreover, this term is not species-specific unless otherwise designated.

As used herein, a "functional derivative or fragment" of a PTH agonist or a PTH antagonist refers to a derivative or fragment of PTH that still substantially retains its function as a PTH agonist or PTH antagonist. Normally, the derivative or fragment retains at least 50% of its PTH agonist or PTH antagonist activity. Preferably, the derivative or fragment retains at least 60%, 70%, 80%, 90%, 95%, 99% and 100% of its PTH agonist or PTH antagonist activity. It is also possible that a functional derivative or fragment of PTH agonist or PTH antagonist has higher PTH agonist or PTH antagonist activity than a parent molecule from which the functional derivative or fragment is derived from.

As used herein, "treatment" means any manner in which the symptoms of a condition, disorder or disease are ameliorated or otherwise beneficially altered. Treatment also encompasses any pharmaceutical use of the compositions herein.

As used herein, "disease or disorder" refers to a pathological condition in an organism resulting from, e.g., infection or genetic defect, and characterized by identifiable symptoms.

As used herein, "adynamic low bone turnover disease" refers to a variety of disorders involving abnormal PTH agonist and/or antagonist levels in a person. This definition is non-limiting in that it does not refer to only one specific disease, it refers to a variety of disorders that may result from abnormal PTH or PTH component levels in a person. As PTH levels are tied to bone turnover rate, abnormally low levels of PTH agonist, abnormally low levels of PTH agonist/antagonist ratios, and abnormally high levels of PTH antagonist may lead to abnormally low bone turnover in a person. In a person, this type of state may indicate the presence of, or susceptibility to, an adynamic low bone turnover disease. Conversely, abnormally high levels of PTH agonist, abnormally high levels of PTH agonist/antagonist ratios, and abnormally low levels of PTH antagonist may lead to abnormally high bone turnover in a person.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "antibody" is used in the broadest sense. Therefore, an "antibody" can be naturally occurring or man-made such as monoclonal antibodies produced by conventional hybridoma technology and/or a functional fragment thereof. Antibodies of the present invention comprise monoclonal and polyclonal antibodies as well as fragments containing the antigen-binding domain and/or one or more complementarity determining regions of these antibodies.

As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, "mammal" refers to any of the mammalian class of species. Frequently, the term "mammal," as used herein, refers to humans, human subjects or human patients.

As used herein, "whole parathyroid hormone (PTH)" or "wPTH" refers to the complete molecule of PTH, e.g., $PTH_{1-84}$. This term is not species-specific unless otherwise designated. For purposes herein, the name "parathyroid hormone (PTH)" is used herein, although all other names are contemplated. It is intended to encompass whole PTH with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. Co., p. 224).

As used herein, the term "PIN" refers to PTH fragments that have PTH antagonistic or inhibiting properties. Therefore, although occasionally of concurrent scope, a reference to PTH fragments, as provided herein, is not intended to be limited to PIN.

As used herein, a "PTH fragment" is a PTH peptide that comprises a non-whole contiguous portion of an entire PTH protein. A reference to a PTH fragment as herein includes C-terminal, mid-terminal fragments and PIN, unless otherwise indicated. Moreover, this term is not species-specific unless otherwise designated.

As used herein, the term "subject" is not limited to a specific species or sample type. For example, the term "subject" may refer to a patient, and frequently a human patient. However, this term is not limited to humans and thus encompasses a variety of mammalian species.

As used herein, "afflicted" as it relates to a disease or disorder refers to a subject having or directly affected by the designated disease or disorder.

As used herein, the term "specifically binds" refers to the specificity of an antibody such that it preferentially binds to a defined target. Recognition by an antibody of a particular target in the presence of other potential targets is one characteristic of such binding. Specific binding of the presently contemplated antibodies to particular PTH targets is measured through known methods utilizing the tools provided herein.

As used herein the term "isolated" refers to material removed from its original environment, and is altered from its natural state. For example, an isolated polypeptide could be coupled to a carrier, and still be "isolated" because that polypeptide is not in its original environment.

As used herein, "therapeutic inactivating antibody" refers to a moiety that interferes with the intended mode of action of a therapeutic agent. Frequently, this interference may comprise a complete inhibition of the intended mode of action, however other results are contemplated. For example, a therapeutic inactivating antibody may reduce or eliminate the efficacy, neutralize, counteract or reverse the intended mode of action of a therapeutic agent. Moreover, a therapeutic inactivating antibody may comprise an antibody that (specifically) binds a therapeutic agent comprising a protein or peptide, e.g., a PTH protein or peptide.

As used herein, "PTH based therapeutic agent" refers to an composition and/or agent having at least a whole PTH molecule and/or a portion of a whole PTH incorporated therein. Nucleic acid as well as amino acid based therapeutic agents are contemplated. Often, the whole PTH molecule and/or portion of a whole PTH comprises the active ingredient in the therapeutic agent. On occasion, any of a variety of excipients are included in or with a therapeutic agent of the present type. Although not seeking to be bound by theory, the agent is considered a therapeutic agent regardless of whether it has intended beneficial effects in a subject with respect to a particular disease or disorder.

Methods

In one embodiment, the present methods are not limited to obtaining samples from a subject at rigid time periods after administration of the PTH based therapeutic agent (PBT). In one example, a sample is obtained about 45 minutes after administration of the PBT. In another example, a sample is obtained about 90 minutes after administration of the PBT. Frequently, a sample is obtained from the subject after an amount of time typically required for PTH levels to fluctuate in a subject after exogenous administration of a PBT. Also frequently, a sample is obtained from the subject after an amount of time typically required for PTH levels to fluctuate, and then stabilize, in a subject after exogenous administration of a PBT. Although not bound by theory, generally the time period between the administration of the PBT and drawing the first sample after administration of the PBT is between about 5 minutes to about 4 hours, or more. Thus, on occasion, such time period between the administration of the PBT to the subject, and drawing the first sample from the subject after administration of the PBT may be about 15 minutes, about 30 minutes, about 45 minutes, about 60 minutes, about 90 minutes, about 120 minutes, about 150 minutes, about 180 minutes, about 210 minutes, or about 240 minutes, or more.

In a frequent embodiment, one or more sample are obtained from the subject prior to administration of the PBT, and one or more samples are obtained from the subject after administration of the PBT. In one aspect, on each occasion a sample is obtained from a subject, such sample may comprise one or more vials or test tubes of a sample. Often, the amount of sample necessary to perform the present methods dictates the amount of sample obtained from the subject. One of skill in the art would understand that certain medical conditions present in a subject may require obtaining a larger volume of sample for that subject versus another subject. For example, when the serum of a sample is assayed, a particular initial volume of serum may be required; in subjects having low serum volumes versus other blood components, a larger amount of sample may be required for these subjects.

The examples provided below illustrate and exemplify several aspects of the present disclosure. However, the present disclosure is not intended to be limited to the disclosed examples. For example, frequently, the PTH based therapeutic is not limited to teraparatide, $PTH_{1-34}$ or FORTEO®. Often, the PTH based therapeutic may comprise a synthetic or purified PTH agonist, as defined herein, as an active ingredient. Alternatively, the PTH based therapeutic may comprise a synthetic or purified PTH antagonist, as defined herein, as an active ingredient. The common aspect of the PTH based therapeutic is that it comprises, at least a portion of a PTH molecule, including, for example, $PTH_{1-84}$ and/or a variety of fragments thereof. On occasion, the PTH based therapeutic comprises at least a portion of a PTH nucleic acid molecule.

In one embodiment, the level of $PTH_{7-84}$ is monitored in a subject both before and after administration of a PTH based therapeutic. In occasional embodiments, the level of $PTH_{7-84}$ is monitored in the subject, if present, irrespective of the levels of total PTH or $PTH_{1-84}$ in the sample. In another occasional embodiment, the level of $PTH_{7-84}$ is monitored in the subject irrespective of the levels of PTH agonists, other PTH antagonists or other PTH fragments that may be nonfunctional if present in the sample.

PTH Ratios

In one embodiment, a method is provided for assessing a subject's candidacy for treatment with a PTH based therapeutic composition comprising: a) obtaining a first biological sample from said subject; b) administering to said subject a parathyroid hormone (PTH) based therapeutic composition; c) obtaining a second biological sample from said subject after administration of said therapeutic; d) determining the level of a parathyroid hormone (PTH) agonist and a PTH antagonist in the first and second samples; e) obtaining a ratio of the PTH agonist versus the PTH antagonist for the first and second samples; and d) comparing the ratios in the first and second samples. Frequently, based on the comparison of the ratios, a therapeutic decision can be made for the subject regarding whether the subject should receive the PTH based therapeutic composition. For example, if the ratio of PTH antagonist in the second sample is higher than the ratio of the PTH antagonist in the first sample then the subject may be considered a candidate for treatment with the PTH based therapeutic composition. As another example, if the ratio of PTH antagonist in the second sample is the same as or lower than the ratio of the PTH antagonist in the first sample then the subject may not be considered a candidate for treatment with the PTH based therapeutic composition.

Also frequently, a third sample is obtained from the subject after the second sample is obtained, and a similar determination is made with regard to the third sample versus the first sample (and optionally the second sample). For example, if the ratio of PTH antagonist versus the total PTH level (or the PTH agonist level) in the third sample is higher than the ratio of the PTH antagonist versus the total PTH level (or the PTH agonist level) in the first and/or second sample, then the subject may be considered a candidate for treatment with the PTH based therapeutic composition. As another example, if the ratio of PTH antagonist versus the total PTH level (or the PTH agonist level) in the third sample is the same as or lower than the ratio of the PTH antagonist versus the total PTH level (or the PTH agonist level) in the first and/or second sample, then the subject may not be considered a candidate for treatment with the PTH based therapeutic composition. If desired the ratio change, if any, may be monitored between each sample and such monitoring may be utilized to guide therapy in the subject in accordance with the methods presented herein.

In an occasional aspect, the PTH antagonist level is determined by determining a total PTH level and determining a PTH agonist level, followed by subtracting the PTH agonist level from the total PTH level. In another occasional aspect, the PTH agonist comprises $PTH_{1-84}$, and the PTH antagonist comprises $PTH_{7-84}$.

In one embodiment, a method is provided for assessing a subject's candidacy for treatment with a PTH based therapeutic composition comprising: a) obtaining a first biological sample from said subject; b) administering to said subject a PTH based therapeutic composition; c) obtaining a second biological sample from said subject after administration of said therapeutic; d) determining the level of a PTH antagonist and a total PTH level in the first and second samples; e) obtaining a ratio of the PTH antagonist level versus the total PTH level for the first and second samples; and d) comparing the ratios in the first and second samples. Frequently, based on the comparison of the ratios, a therapeutic decision can be made for the subject regarding whether the subject should receive the PTH based therapeutic composition. For example, if the ratio of PTH antagonist level versus the total PTH level in the second sample is higher than the ratio of the PTH antagonist level versus the total PTH level in the first sample, then the subject may be considered a candidate for treatment with the PTH based therapeutic composition. As another example, if the ratio of the PTH antagonist level versus the total PTH level in the second sample is the same as or lower than the ratio of the PTH antagonist level versus the total PTH level in the first sample, then the subject may not be considered a candidate for treatment with the PTH based therapeutic composition.

Also frequently, a third sample is obtained from the subject after the second sample is obtained, and a similar determination is made with regard to the third sample versus the first sample (and optionally the second sample). For example, if the ratio of the PTH antagonist level versus the total PTH level in the third sample is higher than the ratio of the PTH antagonist level versus the total PTH level in the first sample, then the subject may be considered a candidate for treatment with the PTH based therapeutic composition. As another example, if the ratio of the PTH antagonist level versus the total PTH level in the third sample is the same as or lower than the ratio of the PTH antagonist level versus the total PTH level in the first sample, then the subject may not be considered a candidate for treatment with the PTH based therapeutic composition. If desired, the ratio change, if any, may be monitored between each sample and such monitoring may be utilized to guide therapy in the subject in accordance with the methods presented herein.

Although the ratios are presented in a specific format, i.e., PTH antagonist versus PTH agonist and/or PTH antagonist versus total PTH, other configurations of the ratio are clearly contemplated. For example, the ratio may be presented as PTH agonist versus PTH antagonist and/or total PTH versus PTH antagonist. The values obtained due to this inverse of parameters are easily calculated and their significance in the context of the present disclosure would be clear to one of skill in the art.

Frequently, the PTH agonist, PTH antagonist, and/or the total PTH levels and the corresponding ratios may be calculated using a Scantibodies Laboratory Whole PTH Assay, Scantibodies Laboratory CAP Assay, Scantibodies Laboratory Intact PTH Assay, Scantibodies Laboratory Total Intact PTH Assay or a combination thereof. PTH-related assays of this type are available from Scantibodies Laboratory, Santee, Calif.

In one aspect, the present description contemplates a variety of PTH assays. Frequently, PTH assays of the present invention comprise immunoassays. A variety of immunoassays are contemplated for use in the presently described methods. Generally, however, the object of any particular assay is to analyze the binding between an analyte, if present in a sample, and one or more immunoreactants. This analysis may be in sandwich assay or competitive assay format or antibody detection assay format. Representative assays may include, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, chemiluminescence assay, lateral flow immunoassay, µ-capture assay, inhibition assay, energy transfer assay, avidity assay, turbidometric immunoassay and time resolved amplified cryptate emission (TRACE) assay.

A variety of patient populations may benefit from the present invention. Generally, without limitation, such populations may be dialysis patients, pre-dialysis patients, end-stage renal disease (ESRD) patients, pre end-stage renal disease (ESRD) persons, or osteoporosis patients. As used herein, a "patient" refers to a person afflicted with, diagnosed, or otherwise suspected as having a particular medical disorder.

In yet another aspect, the parathyroid hormone agonist level of the present invention is determined using an antibody that distinguishes PTH agonist from PTH antagonist. In a related aspect, the parathyroid hormone antagonist level may be determined using an antibody that distinguishes PTH antagonist from PTH agonist. Suitable antibodies include those that are an antibody or an antibody fragment specific for the PTH peptide SER-VAL-SER-GLU-ILE-GLN (SEQ ID NO:2); or antibodies comprising an anti-(1-6) PTH antibody, anti-(1-4) PTH antibody, anti-(1-9) PTH antibody, anti-(1-11) PTH antibody, anti-(1-12) PTH antibody, among others, or a combination thereof.

Therapeutic Inactivating Antibodies

In a frequent embodiment of the present disclosure, methods are provided for the evaluation of a sample for a therapeutic inactivating antibody. Frequently, an antibody of this type is specific for, and/or specifically binds to, a PTH based therapeutic agent or composition. Often, a sample will be evaluated for the presence and/or level of a therapeutic inactivating antibody in addition to evaluating the sample for the level of a PTH antagonist, and optionally the level of a PTH agonist or the total PTH level. Although, on occasion, evaluation of the sample for either a therapeutic inactivating antibody, or evaluating the sample for the level of a PTH antagonist, and optionally the level of a PTH agonist or the total PTH level will be undertaken. Methods useful for the evaluation of a sample for the presence and/or level of a therapeutic inactivating antibody are further described below. See also U.S. application Ser. No. 10/664,263, filed Sep. 16, 2003.

Other features and advantages of the invention will be apparent from the following detailed description.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

In the case of an osteoporosis patient, as PTH (e.g., $PTH_{1-34}$, $PTH_{1-84}$ or functional fragments thereof) is administered, $PTH_{7-84}$ production is stimulated via a biofeedback mechanism. Calcium homeostasis is maintained by the biological actions of $PTH_{1-84}$ and $PTH_{7-84}$; for example, $PTH_{1-84}$ increases bone turnover and $PTH_{7-84}$ decreases bone turnover. These two hormones play a significant role in the net bone turnover which, in turn, controls the serum calcium levels. Therefore, when a $PTH_{1-84}$ (or $PTH_{1-34}$) based therapeutic composition is injected (or otherwise introduced) into a patient, the body responds by increasing bone turnover with a rise in calcium. However, in order to bring both the turnover and the serum calcium level back under control, the body produces $PTH_{7-84}$ in response to the $PTH_{1-84}$ (or $PTH_{1-34}$) intervention. Although not bound by theory, it is believed that this self production of the $PTH_{7-84}$ treats osteoporosis. This biofeedback mechanism is similar to the way the $PTH_{1-84}$/$PTH_{7-84}$ ratio changes in response to an increase in calcium levels. As indicated in Faugere M-C et al., *Kidney Int.* 60:1460-1468 (2001), $PTH_{7-84}$ levels increase relative to $PTH_{1-84}$ levels in response to an increase in circulating calcium levels, thus reducing the ratio of $PTH_{1-84}$/$PTH_{7-84}$.

It is understood that osteoporosis involves bone resorption and that, generally, the treatment for osteoporosis consists of the inhibition of bone resorption. As one example, Salmon Calcitonin (e.g., MIACALCIN®, available from Armour Pharmaceutical Co.) comprises a nasal spray treatment for osteoporosis that is intended to inhibit bone resorption.

Moreover, as is evident in light of Divieti P et al., *Endocrinology* 143(1):171-76 (2002), $PTH_{7-84}$ acts to inhibit bone resorption as well. Similar to bisphosphonates (including, for example, FOSAMAX® (alendronate sodium) (available from Merck & Co., Inc.), EVISTA® (raloxifene hydrochloride) (available from Eli Lilly), etidronate, pamidronate, residronate, teludronate, clodronate, alondronate, etc.), $PTH_{7-84}$ inhibits bone resorption by inhibiting osteoclast formation. See id.; Divieti, P. et al., *J. Bone Miner Res Suppl* 1, S307 (2001); Faugere, M. C. et al., *J Am Soc Nephrol* 12: 764A (2001). However, bisphosphonates accomplish this task by poisoning the osteoclasts (e.g., by inhibiting protein prenylation). See, e.g., van Beek, E. et al., *Biochem. Biophys. Res Commun.* 264:108-111 (1999); Bergstrom, J. et al., *Arch. Biochem. Biophys.* 373:231-241 (2000).

Although not bound by theory, our current understanding is that, surprisingly, the administration of $PTH_{1-34}$ comprises an indirect treatment (through a biofeedback mechanism discussed herein) for osteoporosis via the stimulation of $PTH_{7-84}$ production. As indicated above, $PTH_{7-84}$ inhibits osteoclast formation thus inhibiting bone resorption. Accordingly, the administration of $PTH_{1-34}$ (e.g., FORTEO® (teriparatide) (available from Eli Lilly)) or $PTH_{1-84}$ (e.g., PREOS® (available from NPS Pharmaceuticals)) inhibits bone resorption indirectly through the $PTH_{7-84}$ biofeedback mechanism, rather than, for example, $PTH_{1-34}$ or $PTH_{1-84}$ itself breaking down and building bone. See, e.g., Black D. M. et al., *N Engl. J. Med.* 349:1207-15 (2003).

Although not bound by theory, it is our current understanding that patients that have received administration of a recombinant $PTH_{1-34}$ therapeutic such as FORTEO® for over one year will occasionally become less responsive or non-responsive (i.e., resistant) to this therapeutic. Thus, in these patients, bone resorption would no longer be inhibited by this therapeutic. There appear to be two reasons for the development of resistance to $PTH_{1-34}$ (and specifically FORTEO®) administration (either or both of which may apply). First, a patient receiving administration of this therapeutic may develop antibodies that specifically bind to and inactivate the PTH therapeutic. Second, from a functional viewpoint, the body eventually recognizes that the $PTH_{1-34}$ is foreign and that it should not respond to the exogenous administration of this foreign compound by producing $PTH_{7-84}$. As an additional concern, in rat studies lasting two years, teriparatide (the active ingredient in FORTEO®) caused an increase in the incidence of osteosarcoma, a malignant bone tumor, which was dependent on dose and duration of treatment. However, to date, no case of osteosarcoma has been reported in the patients who received FORTEO® in clinical trials. The currently recommended dosage of FORTEO® for the treatment of osteoporosis comprises a costly daily subcutaneous injection for a maximum of 24 months. Use of FORTEO® over this 24 months period is not recommended as indicated in their FDA approved product insert. Moreover, many health plans will not allow coverage of treatment with FORTEO® beyond 24 months. Thus, this treatment comprises a painful and costly treatment that can be used for what appears to be a maximum of 24 months. As patients with osteoporosis generally live well beyond two years after onset of the disease, an inherent problem is afoot. Other treatment modalities must be considered for patients afflicted with osteoporosis.

Therefore, again not bound by theory, it is our current understanding that monitoring the effectiveness of PTH-based therapeutics, including resistance development to such therapeutics, is important both to ensure that such therapeutics are not inappropriately administered, and to ensure that the most appropriate treatment modality (e.g., PTH related treatment) is utilized for each patient.

Accordingly, the present description provides methods and kits useful to test for a patients' responsiveness to PTH-based therapeutics (i.e., PTH response testing).

For example, in one embodiment, a protocol useful to evaluate a patient for responsiveness to teraparatide $PTH_{1-34}$ is provided by the following. Prior to administration of FORTEO®, a physician retrieves a blood sample from the osteoporosis patient about to receive such treatment. This sample serves as a baseline sample. After retrieving the blood sample the recommended dosage of FORTEO® is administered. At forty five and ninety minutes intervals after administration of the teraparatide composition to the patient, the physician retrieves blood samples from the patient. Plasma is retrieved from each of the three blood samples and optionally frozen in predefined quantities (e.g., 1 ml) for storage and/or transport. Each of the serum samples are then tested for the total PTH levels, $PTH_{1-84}$ levels, $PTH_{7-84}$ levels (see, for example, in U.S. application Ser. No. 09/928,048, filed Aug. 10, 2001 (published as U.S. 2003/0138858 A1), U.S. application Ser. No. 10/265,276, filed Oct. 3, 2002 (published as U.S. 2004/0067526 A1), and U.S. patent application Ser. No. 10/617,489, filed Jul. 10, 2003), and/or for inactivating antibodies specific for the $PTH_{1-34}$ therapeutic (see below; see also U.S. patent application Ser. No. 10/664,263, filed Sep.

16, 2003). Such testing is available at Scantibodies Laboratory, Inc. (Santee, Calif.). In particular, in light of the information provided above regarding the understood role of $PTH_{7-84}$ in bone resorption, the determination of the presence and/or levels of $PTH_{7-84}$ comprises a frequent component of the sample testing. Moreover, the ratio of $PTH_{7-84}$ versus total PTH and/or $PTH_{1-84}$ are also frequently determined.

If the $PTH_{7-84}$ concentration present in the 45 minute and/or 90 minute samples is higher than the $PTH_{7-84}$ concentration in the baseline sample, and/or the ratio of $PTH_{7-84}$ versus total PTH and/or $PTH_{1-84}$ is higher in the 45 minute and/or 90 minute samples versus the ratio of $PTH_{7-84}$ versus total PTH and/or $PTH_{1-84}$ in the baseline sample, then the patient may be a candidate for treatment with FORTEO®. As an optional indication, if there is no evidence of inactivating antibodies specific for the teraparatide therapeutic present in the samples (together with the above information regarding PTH levels and ratios) then the patient may also be considered a candidate for treatment with FORTEO®. However, these considerations may be taken together with those provided by the manufacturer and/or the patient's physician when deciding to initiate treatment with FORTEO®.

If the $PTH_{7-84}$ concentration present in the 45 minute and 90 minute samples is not higher than the $PTH_{7-84}$ concentration in the baseline sample, and/or the ratio of $PTH_{7-84}$ versus total PTH and/or $PTH_{7-84}$ is the same or lower in the 45 minute and/or 90 minute samples versus the ratio of $PTH_{7-84}$ versus total PTH and/or $PTH_{1-84}$ in the baseline samples, then the patient should not be considered a candidate for treatment with FORTEO®. Moreover, as an optional indication, if there is evidence of inactivating antibodies specific for the teraparatide therapeutic present in the samples (together with the above information regarding PTH levels and ratios) then the patient should not be considered a candidate for treatment with FORTEO®.

A selection of alternative therapeutics may be utilized to treat osteoporosis patients. For example, the physician may choose from a bisphosphonate (including, e.g., FOSAMAX® (alendronate sodium) (available from Merck & Co., Inc.), EVISTA® (raloxifene hydrochloride) (available from Eli Lilly), etidronate, pamidronate, residronate, teludronate, clodronate, alondronate, etc.), salmon calcitonin (nasal spray) (i.e., MIACALCIN® (available from Novartis)), CITRACAL® (calcium citrate, and others of the like), $PTH_{1-84}$, and/or $PTH_{7-84}$ administration. As each of these compositions present their own health-related concerns, it would be advisable for the physician to consider the following information:

With regard to bisphosphonates, numerous issues should be considered. For example, many patients have stomach intolerance for bisphosphonates. And, more importantly, as these compositions become permanently incorporated into the bone, they will act as a future poison against osteoclast formation. For example, recent evidence has indicated that treatment with bisphosphanates may result in a substantial decrease (up to 90%) in collagen synthesis and over mineralized bone (i.e., osteopetrosis). See Whyte M. P. et al., *N. Engl. J. Med.* 349:457-63 (2003). Further, treatment with bisphosphanates may result in the patient becoming nonresponsive to PTH-based therapeutics. See, e.g., Zikan V, Stepan J J, *Clin. Chim. Acta* 316:63-9 (2002). Thus, concurrent treatment with bisphosphanates and PTH-based therapeutics should be avoided. Moreover, although not bound by any particular theory, as there is a possibility that the patient may lose to ability to achieve bone turnover as a result of bisphosphanate treatment, it appears that these should be utilized only after PTH-based therapeutic options are exhausted. Notably, this recommendation is in stark contrast to the recommended patient criteria for the use of FORTEO®. For example, it is recommended that bisphosphanate treatment related options are exhausted (by intolerance or ineffectiveness) prior to utilizing FORTEO®. See, e.g., Black D. M. et al., *N Engl. J. Med.* 349:1207-15 (2003).

As for the use of salmon calcitonin, this therapeutic is generally utilized in the form of a nasal spray, to which many patients develop irritation. Moreover, 16% of the patients develop a down regulation of the calcitonin receptors after prolonged treatment, which results in a resistance to this therapeutic. For example, after 5 years or less of treatment, most patients become resistant and no longer respond. See, e.g., Grauer A et al., *Dtsch. Med. Wochenschr.* 119:507-10 (1994). CITRACAL® (calcium citrate) presents another therapeutic option.

The use of therapeutic compositions comprising $PTH_{1-84}$ (i.e., PREOS®) and/or $PTH_{7-84}$ in the treatment of osteoporosis may present similar problems and risks to those set out above pertaining to the use of $PTH_{1-34}$ to treat osteoporosis. As such, a similar testing scheme is contemplated and presented herein to determine whether a particular patient is a candidate for treatment with therapeutic compositions comprising $PTH_{1-84}$ (i.e., PREOS®) and/or $PTH_{7-84}$.

Example 2

A first blood sample (2×5 ml in EDTA) is obtained from a subject diagnosed as having, or suspected of having, osteoporosis. Serum is separated from the first sample and frozen in 1 ml aliquots. A therapeutic composition comprising $PTH_{1-34}$ is then administered (20 mcg SC QD) to the subject. Forty five minutes after administration of the therapeutic composition, a second blood sample (2×5 ml in EDTA) is retrieved from the subject. Serum is separated from the second sample and frozen in 1 ml aliquots. Ninety minutes after administration of the therapeutic composition, a third blood sample (2×5 ml in EDTA) is retrieved from the subject. Serum is separated from the third sample and frozen in 1 ml aliquots. Each of the three samples are then tested for the concentration of total PTH, $PTH_{1-84}$ and $PTH_{7-84}$ utilizing protocols set out, for example, in U.S. application Ser. No. 09/928,048, filed Aug. 10, 2001 (published as U.S. 2003/0138858 A1), U.S. application Ser. No. 10/265,276, filed Oct. 3, 2002 (published as U.S. 2004/0067526 A1), and U.S. patent application Ser. No. 10/617,489, filed Jul. 10, 2003 (such testing is available at Scantibodies Laboratory, Inc.). Each of the three samples is also tested for the presence and/or concentrations of antibodies that specifically bind (and inactivate) the therapeutic composition comprising $PTH_{1-34}$ by the following method.

Human antibody that is capable of specifically binding an antigen is separated from each of the serum samples for evaluation. This human antibody is separated from the sample through the formation of a reaction mixture and removal of the antibody, if present. The reaction mixture is formed via the introduction of a labeled and unhindered antigen comprising a $PTH_{1-34}$ composition to the patient sample and allowing the human antibody specific for the $PTH_{1-34}$ composition, if present, bind thereto. The $PTH_{1-34}$ composition is labeled utilizing an Iodine-125 labeled (or optionally luminol) and is unhindered in that it is not attached to a solid substrate. See, e.g., U.S. patent application Ser. No. 10/664,263, filed Sep. 16, 2003. Additionally, goat anti-human IgG is introduced to the mixture of human antibody and labeled unhindered $PTH_{1-34}$ after the human antibody is allowed to bind the labeled unhindered $PTH_{1-34}$ to form a labeled complex. The human antibody comprised in the complex is then separated from the reaction mixture via precipitation. The complex is precipitated from the reaction mixture via centrifugation and aspirating or decanting the supernatant. Optionally, the reaction mixture is diluted utilizing a buffer prior to centrifugation. Also optionally, a detergent (e.g., Tween-20) is added to the reaction mixture prior to centrifugation. The precipitated labeled complex is then assessed for the presence and/or concentration of label. In the case of the use of Iodine-125 as a label, the precipitated labeled complex is assessed utilizing a gamma counter. In one aspect, the labeled and unhindered antigen comprising a $PTH_{1-34}$ will often consist of a labeled and unhindered form of the $PTH_{1-34}$ therapeutic composition previously administered to the subject.

If human antibody is detected that is specific for the $PTH_{1-34}$ therapeutic composition then therapeutic inactivating antibodies specific for the $PTH_{1-34}$ therapeutic composition are determined to be present.

Example 3

In accordance with the methods provided in Example 2, a first blood sample (2×5 ml in EDTA) is obtained from a subject diagnosed as having, or suspected of having, osteoporosis. Serum is separated from the first sample and frozen in 1 ml aliquots. A therapeutic composition comprising $PTH_{1-84}$ is then administered (20 mcg SC QD) to the subject. Forty five minutes after administration of the therapeutic composition, a second blood sample (2×5 ml in EDTA) is retrieved from the subject. Serum is separated from the second sample and frozen in 1 ml aliquots. Ninety minutes after administration of the therapeutic composition, a third blood sample (2×5 ml in EDTA) is retrieved from the subject. Serum is separated from the third sample and frozen in 1 ml aliquots. Each of the three samples are then tested for the concentration of total PTH, $PTH_{1-84}$ and $PTH_{7-84}$ utilizing protocols as referenced above (such testing is available at Scantibodies Laboratory, Inc.). Each of the three samples are also tested for the presence and/or concentrations of antibodies that specifically bind (and inactivate) the therapeutic composition comprising $PTH_{1-84}$ by the following method.

Human antibody that is capable of specifically binding an antigen is separated from each of the serum samples for evaluation. This human antibody is separated from the sample through the formation of a reaction mixture and removal of the antibody, if present. The reaction mixture is formed via the introduction of a labeled and unhindered antigen comprising a $PTH_{1-84}$ composition to the patient sample and allowing the human antibody specific for the $PTH_{1-84}$ composition, if present, bind thereto. The $PTH_{1-84}$ composition is labeled utilizing an Iodine-125 labeled (or optionally luminol) and is unhindered in that it is not attached to a solid substrate. See, e.g., U.S. patent application Ser. No. 10/664,263, filed Sep. 16, 2003. Additionally, goat anti-human IgG is introduced to the mixture of human antibody and labeled unhindered $PTH_{1-84}$ after the human antibody is allowed to bind the labeled unhindered $PTH_{1-84}$ to form a labeled complex. The human antibody comprised in the complex is then separated from the reaction mixture via precipitation. The complex is precipitated from the reaction mixture via centrifugation and aspirating or decanting the supernatant. Optionally, the reaction mixture is diluted utilizing a buffer prior to centrifugation. Also optionally, a detergent (e.g., Tween-20) is added to the reaction mixture prior to centrifugation. The precipitated labeled complex is then assessed for the presence and/or concentration of label. In the case of the use of Iodine-125 as a label, the precipitated labeled complex is assessed utilizing a gamma counter. In one aspect, the labeled and unhindered antigen comprising a $PTH_{1-84}$ will often consist of a labeled and unhindered form of the $PTH_{1-84}$ therapeutic composition previously administered to the subject.

If human antibody is detected that is specific for the $PTH_{1-84}$ therapeutic composition then therapeutic inactivating antibodies specific for the $PTH_{1-84}$ therapeutic composition are determined to be present.

Example 4

In accordance with the methods provided in Examples 2 and 3, a first blood sample (2×5 ml in EDTA) is obtained from a subject diagnosed as having, or suspected of having, osteoporosis. Serum is separated from the first sample and frozen in 1 ml aliquots. A therapeutic composition comprising $PTH_{7-84}$ is then administered (20 mcg SC QD) to the subject. Forty five minutes after administration of the therapeutic composition, a second blood sample (2×5 ml in EDTA) is retrieved from the subject. Serum is separated from the second sample and frozen in 1 ml aliquots. Ninety minutes after administration of the therapeutic composition, a third blood sample (2×5 ml in EDTA) is retrieved from the subject. Serum is separated from the third sample and frozen in 1 ml aliquots. Each of the three samples are then tested for the concentration of total PTH, $PTH_{1-84}$ and $PTH_{7-84}$ utilizing protocols as referenced above (such testing is available at Scantibodies Laboratory, Inc.). Each of the three samples are also tested for the presence and/or concentrations of antibodies that specifically bind (and inactivate) the therapeutic composition comprising $PTH_{7-84}$ by the following method.

Human antibody that is capable of specifically binding an antigen is separated from each of the serum samples for evaluation. This human antibody is separated from the sample through the formation of a reaction mixture and removal of the antibody, if present. The reaction mixture is formed via the introduction of a labeled and unhindered antigen comprising a $PTH_{7-84}$ composition to the patient sample and allowing the human antibody specific for the $PTH_{7-84}$ composition, if present, bind thereto. The $PTH_{7-84}$ composition is labeled utilizing an Iodine-125 labeled (or optionally luminol) and is unhindered in that it is not attached to a solid substrate. See, e.g., U.S. patent application Ser. No. 10/664,263, filed Sep. 16, 2003. Additionally, goat anti-human IgG is introduced to the mixture of human antibody and labeled unhindered $PTH_{7-84}$ after the human antibody is allowed to bind the labeled unhindered $PTH_{7-84}$ to form a labeled complex. The human antibody comprised in the complex is then separated from the reaction mixture via precipitation. The complex is precipitated from the reaction mixture via centrifugation and aspirating or decanting the supernatant. Optionally, the reaction mixture is diluted utilizing a buffer prior to centrifugation. Also optionally, a detergent (e.g., Tween-20) is added to the reaction mixture prior to centrifugation. The precipitated labeled complex is then assessed for the presence and/or concentration of label. In the case of the use of Iodine-125 as a label, the precipitated labeled complex is assessed utilizing a gamma counter. In one aspect, the labeled and unhindered antigen comprising a $PTH_{7-84}$ will often consist of a labeled and unhindered form of the $PTH_{7-84}$ therapeutic composition previously administered to the subject.

If human antibody is detected that is specific for the $PTH_{7-84}$ therapeutic composition then therapeutic inactivating antibodies specific for the $PTH_{7-84}$ therapeutic composition are determined to be present.

The above examples are included for illustrative purposes only and are not intended to limit the scope of the invention.

Many variations to those described above are possible. Since modifications and variations to the examples described above will be apparent to those of skill in this art.

Citation of the above publications or documents is not intended as an admission that any of the foregoing is pertinent prior art, nor does it constitute any admission as to the contents or date of these publications or documents.

PTH level or the PTH1-84 level is the same or lower in the second sample versus the first sample, then the subject is not considered a candidate for treatment with said PTH based therapeutic composition.

2. The method of claim 1, wherein the first and second samples are evaluated for two or more parameters comprising

---

---

What is claimed is:

1. A method for guiding administration of a therapeutic agent in a subject afflicted with osteoporosis, comprising:
   a) obtaining a first biological sample from the subject;
   b) administering to said subject a parathyroid hormone (PTH) based therapeutic composition comprising PTH1-84 or PTH1-34;
   c) obtaining a second biological sample from said subject after administration of said therapeutic; and
   d) evaluating said first and second samples for a PTH antagonist level, and optionally a total PTH level or a PTH1-84 level, wherein the PTH antagonist is PTH7-84,
   wherein if the PTH antagonist is present at a higher level in the second sample versus the first sample, and/or if the ratio of the PTH antagonist versus the total PTH level or the PTH1-84 level is higher in the second sample versus the first sample, then the subject may be considered a candidate for treatment with said PTH based therapeutic composition, and
   wherein, if the PTH antagonist is present at the same or lower level in the second sample versus the first sample, and/or if the ratio of the PTH antagonist level versus total the PTH antagonist level, the total PTH level and/or the PTH1-84 level, and at least two of the parameters are compared.

3. The method of claim 2, wherein the two or more parameters are compared in the form of a ratio or proportion.

4. The method of claim 1, wherein a time period exists between the administering step and obtaining the second biological sample, wherein the time period ranges between about 5 minutes to about 4 hours.

5. The method of claim 1, wherein at least one of the steps a)-d) is performed at a different location and/or by a different person or entity from at least one other of the steps a)-d) of claim 1.

6. The method of claim 1, further comprising evaluating the first and second samples for the presence of a therapeutic inactivating antibody specific for the PTH based therapeutic composition, wherein if the therapeutic inactivating antibody specific for the PTH based therapeutic agent is present, the subject is not considered a candidate for treatment with the PTH based therapeutic composition.

7. The method of claim 1, further comprising administering said PTH based therapeutic composition to said subject if said subject is considered a candidate for treatment with said PTH based therapeutic composition according to step d, or administering a therapeutic agent selected from the group consisting of a bisphosphonate, salmon calcitonin, calcium citrate, and a calcimimetic to said subject if said subject is not considered a candidate for treatment with said PTH based therapeutic composition according to step d.

8. The method of claim 7, wherein the calcimimetic is cinacalcet HCl or AMG-073.

9. The method of claim 1, wherein the subject is determined not to be a candidate for treatment with a PTH based therapeutic agent and the method further comprises administering a therapeutic agent selected from a bisphosphonate, salmon calcitonin, calcium citrate, a calcimimetic, or a combination thereof.

10. The method of claim 1, further comprising obtaining a third biological sample from said subject after obtaining the second biological sample, and evaluating said third sample for a PTH antagonist level, and optionally a total PTH level or a PTH1-84 level, wherein the PTH antagonist is PTH1-84, wherein if the PTH antagonist is present at a higher level in the third sample versus the first sample and/or the second sample, and/or if the ratio of the PTH antagonist versus the total PTH level or the PTH1-84 level is higher in the third sample versus the first sample and/or the second sample, then the subject may be considered a candidate for treatment with said PTH based therapeutic composition, and wherein if the PTH antagonist is present at the same or lower level in the third sample versus the first sample and/or the second sample, and/or if the ratio of the PTH antagonist level versus total PTH level (or the PTH1-84 level) is the same or lower in the third sample versus the first sample and/or the second sample, then the subject is not considered a candidate for treatment with said PTH based therapeutic composition.

11. The method of claim 10, wherein the first and third samples are evaluated for two or more parameters comprising the PTH antagonist level, the total PTH level and/or the PTH1-84 level, and at least two of the parameters are compared.

12. The method of claim 11, wherein the two or more parameters are compared in the form of a ratio or proportion.

13. The method of claim 10, wherein a second time period exists between obtaining the second biological sample and obtaining the third biological sample, wherein the second time period ranges between about 5 minutes to about 4 hours.

* * * * *